(12) United States Patent
Hogdahl

(10) Patent No.: US 9,072,838 B2
(45) Date of Patent: Jul. 7, 2015

(54) MEDICAMENT DELIVERY DEVICE

(75) Inventor: Stefan Hogdahl, Stockholm (SE)

(73) Assignee: SHL Group AB, Nacka Strand (SE)

(*) Notice: Subject to any disclaimer, the term of this patent is extended or adjusted under 35 U.S.C. 154(b) by 0 days.

(21) Appl. No.: 14/006,865

(22) PCT Filed: Mar. 13, 2012

(86) PCT No.: PCT/SE2012/050277
§ 371 (c)(1),
(2), (4) Date: Dec. 3, 2013

(87) PCT Pub. No.: WO2012/128699
PCT Pub. Date: Sep. 27, 2012

(65) Prior Publication Data
US 2014/0107587 A1   Apr. 17, 2014

Related U.S. Application Data

(60) Provisional application No. 61/467,061, filed on Mar. 24, 2011.

(30) Foreign Application Priority Data

Mar. 24, 2011 (SE) ........................ 1150264

(51) Int. Cl.
*A61M 5/315* (2006.01)
*A61M 5/20* (2006.01)
*A61M 5/31* (2006.01)
A61M 5/24 (2006.01)

(52) U.S. Cl.
CPC .............. *A61M 5/31591* (2013.01); *A61M 5/20* (2013.01); *A61M 5/3146* (2013.01); *A61M 5/31543* (2013.01); *A61M 5/31553* (2013.01); *A61M 5/31583* (2013.01); A61M 2005/2407 (2013.01); A61M 2005/2477 (2013.01); A61M 2005/2488 (2013.01); *A61M 5/2033* (2013.01)

(58) Field of Classification Search
CPC .............. A61M 5/20; A61M 5/31553; A61M 5/31583; A61M 5/3155; A61M 5/2033; A61M 2005/206; A61M 5/31501; A61M 2005/2407; A61M 2005/2488; A61M 5/3146; A61M 5/31591; A61M 5/31525; A61M 5/31543; A61M 2005/2477; A61M 5/31511; A61M 5/24; A61M 5/3129
USPC ........................................................ 604/228
See application file for complete search history.

(56) References Cited

U.S. PATENT DOCUMENTS

2002/0095120 A1    7/2002 Larsen et al.

FOREIGN PATENT DOCUMENTS

| WO | 01/10484 A1 | 2/2001 |
|---|---|---|
| WO | 2009/101005 A1 | 8/2009 |
| WO | WO 2009101005 A1 * | 8/2009 |
| WO | 2010/029043 A1 | 3/2010 |

* cited by examiner

*Primary Examiner* — Jason Flick
(74) *Attorney, Agent, or Firm* — McDonnell Boehnen Hulbert & Berghoff LLP

(57) ABSTRACT

The present invention relates to a medicament delivery device comprising a distal housing part (12), and a proximal housing part (10) adapted to receive a medicament container (14) comprising a movable stopper (15), wherein said housing parts are configured to be attached to each other; a threaded plunger rod (22) arranged within said medicament delivery device and being movable in the longitudinal direction of the device; wherein the medicament delivery device further comprises plunger force means (98) operably associated with said threaded plunger rod (22) and configured to exert both a torsion force and a tension force on said threaded plunger rod (22) for positioning the plunger rod in relation to the stopper and for avoiding drooling respectively.

15 Claims, 10 Drawing Sheets

MEDICAMENT DELIVERY DEVICE

TECHNICAL FIELD

The present invention relates to a medicament delivery device and in particular a device where unwanted expelling of medicament after delivery may occur.

BACKGROUND OF THE INVENTION

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a delivery member attached to the opposite end of the compartment, such as e.g. a needle, a nozzle or the like member capable of delivering medicament to a patient.

In order to deliver a quantity of medicament, the stopper is exposed to pressure, i.e. pushed into the compartment by a plunger rod, which could be done manually by a finger, which is the case for simple handheld syringes, or by pressure means such as springs, which is common in automatic or semi-automatic injectors.

In many instances it is desirable to be able to deliver a certain specified quantity of the medicament. This is for example the case with a multi-dose injection device, which is capable of delivering a number of specified, set, doses until the compartment is empty. One example is disclosed in the European patent application No. 05/104,734.8 where specific doses can be set before injection. The injection device disclosed is arranged with spring means for exerting a pressure on the medicament for delivering a specific dose, i.e. pushing the plunger rod and thus the stopper into the container.

The delivery of a dose requires a certain force from the spring means in order to overcome the friction between the somewhat resilient stopper and the inner surface of the cartridge and also to be able to press the medicament in liquid form through a rather small passage in the delivery member, possibly within a predetermined time.

Due to the elasticity of the components under pressure such as the stopper and also the medicament if non-newtonian, there is a prevailing pressure even when the stopper has been moved a predetermined distance and the dose has been delivered. This is in particular pronounced when handling medicament with rather high viscosity, medicament having resilient properties.

With this type of substance with high viscosity, and because very small passages of the delivery member often are used, a rather large force is required and because of the elasticity of the components, often a certain small quantity of the substance comes out of the delivery member even after performed delivery when the pressure is relieved, i.e. there is some dripping from the delivery member, which is unwanted, in particular when treating a patient and the substance may be dripping on the patient's skin, possibly causing irritation or inconvenient, undesirable effects.

One solution is disclosed in WO 2008/020,023 A1. The device of WO 2008/020,023 A1 comprises a mechanism which causes the plunger rod to move in the distal direction in order to release any remaining pressure after a dose delivery. The mechanism could comprise ratchets cooperating with each other or a "wave-shaped" surface on which rollers move, all in order to create a movement in the distal direction of the plunger rod.

The drawback with the solution according to WO 2008/020,023 A1 is that there are mechanical components that are to interact with each other, which on the one hand will cause noise and vibrations and on the other hand can lead to increased friction that has to be handled with larger and stronger springs.

The plunger rods of many medicament delivery devices are threaded and cooperate with threaded nuts whereby either the plunger rod is rotated or the nut is rotated when advancing the plunger rod. For disposable medicament delivery devices this solution works very well because when the plunger rod has moved to its most forward position, the medicament container is empty and the medicament delivery device can be discarded. However, for reusable medicament delivery devices which use an auto-mechanism for delivering a dose of medicament, there is a problem when using threaded plunger rods because they have to be threaded back to their original position. One example is disclosed in EP 0937471 A1 showing a pen injector where a threaded plunger rod is threaded back to its original position.

This operation is not appreciated by most users, and may also lead to wrong handling of the device in that there could be an uncertainty as to how far the plunger rod should be threaded back. Further, there are a number of medicament delivery devices where the delivery mechanisms, and mechanisms associated with the delivery, do not permit a return of the plunger rod.

There is thus room for developments regarding handling of pressure release situations with medicament delivery devices in order to avoid drooling.

BRIEF DESCRIPTION OF THE INVENTION

The aim of the present invention is to provide a medicament delivery device wherein any unintentional delivery of medicament after use, so called drooling, is prevented or at least minimized as well as handling the positioning of a plunger rod in relation to a stopper of a medicament container when a medicament container is positioned within the medicament delivery device.

This aim is obtained by a medicament delivery device according to the features of the independent patent claim. Preferable embodiments of the invention form subject of the dependent patent claims.

According to a main aspect of the invention, the medicament delivery device comprises a distal housing part, and a proximal housing part adapted to receive a medicament container comprising a movable stopper at its distal end, wherein said housing parts are configured to be attached to each other; and a threaded plunger rod arranged within said medicament delivery device and being movable in the longitudinal direction of the device. Furthermore a plunger force means is operably associated with said threaded plunger rod and configured to exert both a torsion force and a tension force on said threaded plunger rod for positioning the plunger rod in relation to the stopper and for avoiding drooling respectively.

The proximal housing part is preferably arranged as a medicament container holder which accommodates a medicament container. The medicament container may be arranged with a movable stopper of a resilient material enclosing a distal end of the medicament container. The medicament container holder may be arranged with a neck at its proximal end for attaching, e.g., an injection needle.

It is preferred that the housing parts comprise suitable attachment means such as bayonet fittings, threads, or the like for attaching the proximal housing part with the distal housing part.

The elongated and threaded plunger rod may be arranged inside the distal housing part. The plunger rod has a longitudinal axis which generally corresponds with the longitudinal axis or direction of the medicament delivery device. According to an embodiment of the invention, the plunger rod comprises threads on its outer surface as well as longitudinally extending grooves. The grooves also located on the outer surface of the rod are positioned on opposite sides of the rod as seen in a transversal direction of the rod. For example, the threaded plunger rod comprises two, three or four opposing longitudinal grooves.

According to a preferred embodiment, the medicament delivery device further comprises a drive nut configured to drive said threaded plunger rod towards the proximal end of the device. Furthermore, the medicament delivery device comprises drive force means configured to drive said drive nut.

The drive nut is configured to drive/move/displace the plunger rod. Is has a proximal end surface in contact with a wall of the distal housing part. The wall of the distal housing part is preferably located in a proximal area of the distal housing part extends transversally to the longitudinal axis of the device. The wall is provided with a central opening through which the threaded plunger rod extends.

The drive nut is arranged to the threaded plunger rod. For example, the threaded plunger rod and the drive nut are arranged concentrical. In this example, the drive nut is provided with a central opening extending in longitudinal direction of the drive nut. The threaded plunger rod extends through the central opening. Furthermore, the drive nut comprises one or more threads at least at a circumferential part and at least at a longitudinal part of the surface of the inner surface of the central opening. The one or more threads are of a corresponding shape and pitch as the threads of the threaded plunger rod. Hence, the threads of the rod are engageable by the counter-threads of the drive nut when the plunger rod is arranged such that it extends through the central opening. In other words, the drive nut is in threaded engagement with the plunger rod.

The drive force means is configured to drive the drive nut. The drive force means may comprise a preferably elongated drive shaft of substantially cylindrical configuration, a torsion drive spring, a proximal spring attachment member, and a distal spring attachment member.

According to an embodiment of the invention, the distal end of the drive nut is operably connected to the drive shaft. The connection between the drive nut and the drive shaft comprises an inner circumferential surface on the drive nut being provided with a number of wedge-shaped protrusions. The inner circumferential surface is preferably located at the distal end of the drive nut. The wedge-shaped protrusions extend from the inner circumferential surface towards the center axis of the drive nut, i.e. towards the center of central opening. Furthermore, the wedge-shaped protrusions extend teeth-like in longitudinal direction of the drive nut. Preferably, the protrusions are equidistant.

The wedge-shaped protrusions are arranged and shaped to cooperate, for example, with arms arranged at a proximal end of the drive shaft. The arms may extend in a circumferential direction transversal to the longitudinal direction of the drive shaft. That is, the arms may have a curved shape and extend in a plane being perpendicular to the longitudinal axis of the device. The free ends of the arms are arranged with radially outwardly extending protrusions, which protrusions are in contact with, i.e. in operable interaction or engagement with the wedge-shaped protrusions of the drive nut. The preferably curved arms are on one of their ends fixed to or connected with the outer surface of the drive shaft, whereas the other end of each arm is free. Thus, the arms can be deflected towards the surface of the drive shaft depending on the spacing between the free end of the arm and the outer surface of the drive shaft.

Such design of the connection enables rotational movement of the drive shaft in one direction relative the drive nut (wherein the arm(s) deflect towards the surface of the drive shaft), but a rotational lock between the drive shaft and the drive nut in the opposite rotational direction. Such opposite rotational directions would cause the arms to deflect away from the drive shaft surface which is however prevented by the engagement of the protrusions with the wedge-shaped protrusions. In a preferred embodiment, the drive shaft comprises at least one arm, while alternative embodiments have two or three arms.

According to a preferred embodiment, the medicament delivery device comprises a guide member rotatably lockable but longitudinally slidably connected to said threaded plunger rod and configured to be switched by a lock and release mechanism between a locked state in which the guide member is prevented to rotate when said housing parts are connected to each other and a released state in which the guide member is allowed to rotate when said housing parts are disconnected.

The guide member may be arranged with a central longitudinal passage in which central passage the threaded plunger rod further fits into. The central passage may be arranged with guides such as radially inwardly directed protrusions and extending in longitudinal direction of the guide member. The guides have a shape complementary to the grooves of the threaded plunger rod such as to allow a movement of the plunger rod along the guides in the longitudinal direction but to prevent rotation of the threaded plunger rod. An outer circumferential surface of the guide member is arranged with splines or the like ridges, preferably wedge-shaped.

The torsion force acting on the threaded plunger rod when said guide member is in the released state, exceeds the tension force such that said threaded plunger rod is urged towards the proximal end of the device, and wherein the tension force acting on said threaded plunger rod when said guide member is in the locked state exceeds the torsion force such that the threaded plunger rod is urged towards the distal end of the device.

As mentioned above, said threaded plunger rod is configured to act on said stopper.

According to another aspect of the invention, said plunger force means comprises a spring member which is pre-tensioned and twisted arranged inside the threaded plunger rod, and wherein the plunger force means comprises a spring member has a proximal end attached to a proximal part and a distal end attached to a support member.

According to yet an aspect of the invention, said spring member further displays pulling and torsion properties.

According to yet another aspect of the invention, said spring member is a tension spring.

According a preferred embodiment of the invention, the spring member of the plunger rod force means (hereafter named plunger rod control spring) is pre-tensioned and twisted arranged inside an elongated cavity of the threaded plunger rod. A proximal part of the threaded plunger rod or a fixation member comprised in the plunger force means may be attached to the proximal end of the threaded plunger rod, to which fixation member the proximal end of the plunger rod control spring is attached. At a proximal end of the fixation member, a spinner may be rotatably arranged.

Further the distal end of the plunger rod control spring may be attached to a support member, which in its turn can be attached to the drive force. The support member is arranged extending into the cavity from the distal end of the threaded plunger rod. The support member may comprise a guide pin that extends from the support member in the proximal direction inside the plunger rod control spring. The function of the guide pin is to prevent buckling of the plunger rod control spring.

The support member may further comprise two oppositely positioned and transversally extending beams. The beams are arranged and designed such that they fit between two of the arms of the drive shaft, i.e. in the gap between the two arms, when the arms extend through the distal spring attachment member such that the position of the arms are locked in relation to the distal spring attachment member. Thus the support member is also locked to the distal spring attachment member and thus to the drive shaft.

As mentioned above, the plunger rod control spring may be a tension spring and is chosen such that when the device is assembled, the tension spring displays pulling and torsion properties. When the threaded plunger rod is in an initial, most distal, position, the plunger rod control spring causes a pulling force of the threaded plunger rod in the distal direction all the way from its initial most distal position to its most extended proximal position. Further, the plunger rod control spring has been twisted during assembly of the device by turning the support member in relation to the drive shaft and the distal attachment member before the beams of the support member are locked between the arms of the drive shaft. The twisting of the plunger rod control spring is set such that the torsional force acts on the threaded plunger rod to urge it in the proximal direction all the way from its most extended proximal position to its initial, most distal, position.

According to another aspect of the invention, the device further comprises an actuation mechanism is operably connected to said drive nut such that said drive nut is locked when said guide member is in the released state.

According to a further aspect of the invention, said actuation mechanism further comprises a manually operable actuation member, capable of, upon operation, releasing said drive nut and thus said drive means for driving said threaded plunger rod towards the proximal end of the device.

According to a final aspect of the invention, said medicament delivery device is a reusable auto-injector.

The actuating mechanism, for example, comprises circumferentially extending teeth or protrusions on the outer surface of the drive nut. These teeth are arranged to cooperate with mating teeth or protrusions on an inner surface of a ring-shaped member comprised in the actuation mechanism. The actuation mechanism further may comprise a manually operated actuation member in the form of a plate or slide button, to which the ring-shaped member is attached. The actuation member is preferably placed on the outer surface of the distal housing part for access by a user. The actuation mechanism can further comprise a spring arranged between the wall and the ring-shaped member, urging the ring-shaped member in the distal direction and thereby in engagement with the drive nut.

Preferably, a proximal part of said proximal fixation member is connected with the proximal end of the threaded plunger rod. Furthermore, the support member may be connected to said drive force means.

According to a preferred embodiment, the medicament delivery device comprises a rotatable drive shaft and a torsion drive spring, wherein rotation of the drive shaft induced by a user causes said torsion drive spring to tension. The torsion drive spring force acts on said threaded plunger rod in that actuation of the medicament delivery device by the user causes the threaded plunger rod to move in longitudinal direction on account of the tension of said torsion drive spring.

The torsion drive spring of the drive means may be wound surrounding the outer surface of the drive shaft. A proximal end of the torsion drive spring is attached, for example, to the proximal spring attachment member, positioned adjacent and distally of the drive nut. The proximal spring attachment member is fixed to the distal housing part by snap-in tongues, gripping into suitable cut-outs of the distal housing part. Thus, while the proximal spring attachment member is located distally of the drive nut, the drive shaft proximally projects from the proximal spring attachment member in that the arms at the proximal end of the drive shaft extend into the central opening of the drive nut in order to engage with the wedge-shaped protrusions of the drive nut. Thus, the proximal spring attachment member is a ring-like element, and the drive shaft passes therethrough.

The torsion drive spring of the drive force means is also provided with a distal end that may be attached to a distal spring attachment member. The distal spring attachment member comprises, e.g., a circular body arranged with one or more passages. These passages extend through the distal spring attachment member in longitudinal direction of the device, i.e. from proximal to distal (or vice versa). The drive shaft comprises at its distal end distally extending arms, preferably flush with the outer surface of the cylindrical drive shaft. Thus, the distally extending arms have a cross-sectional shape, seen in a plane perpendicular to the longitudinal axis of the device, being ring-segment shaped, i.e. curved or rounded. The distally extending arms of the drive shaft pass through some of these passages. The passages are preferably as well curved around the center axis. The distal ends of the arms are arranged with transversally directed ledges such that when the arms have been positioned in the passages, the ledges contact surfaces of the distal spring attachment member so as to lock the distal spring attachment member to the drive shaft. In other words, the drive shaft is snapped onto the distal spring attachment member. In one embodiment, two arms extend through one passage, forming a first arm pair, and another two arms pass through another passage forming a second arm pair. For each pair of arms, the ledges extend in opposite directions so that they engage opposing ends of the passage. Between the two arms of each pair there is a gap allowing the arms to deflect towards each other when pushed through the passage.

The distal spring attachment member may further operably attached to a drive spring tensioner comprising a knob. The knob may be arranged at the distal end of the device such that when the knob is turned, the distal spring attachment member and the drive shaft are turned in relation to the proximal spring attachment member (being fixedly connected to distal housing part) as well as the drive nut, the latter due to the connection between the drive shaft and the drive nut. The turning action of the knob thus causes a tensioning of the drive spring because the drive spring is on one end connected with the distal spring attachment member which is turned and the on the other end connected to the proximal spring attachment member which is fixed.

The medicament delivery device further comprises a lock and release mechanism. The mechanism may comprise a generally tubular body which is positioned to surround the splines of the guide member. The tubular body preferably comprises two or four oppositely positioned arms. The arms extend generally in the circumferential direction of the tubular body and are flexible in the generally radial direction of the body. On the inwardly directed surfaces of the arms, a number of protrusions, preferably wedge-shaped, are arranged. The protrusions preferably have complementary profiles to the splines of the guide member. On each of the outwardly directed surfaces of the arms, a generally radially outwardly directed ledge may be arranged. The ledges are designed and configured such that they come in contact with an inner surface of the medicament container holder when the medicament container holder is attached to the distal housing part such that the arms are forced radially inwards.

Further the lock and release mechanism may be provided with a ring-shaped resilient member positioned in the interior of the body. The resilient member may be made of metal having resilient properties. The resilient member may have circumferentially extending tongues, which tongues are positioned radially inside the arms of the body and act to support the arms in flexing those outwards in the radial direction.

The body of the lock and release mechanism extends in the proximal direction with a proximal tubular part which is comprised in a medicament container positioner mechanism. The medicament container positioner mechanism may comprise a tubularly shaped pusher member, preferably arranged movable in the longitudinal direction inside the proximal tubular part. The pusher member can be arranged with a number of protrusions on its outer surface in circumferential direction in a plane transverse to the longitudinal axis. These protrusions preferably fit into correspondingly arranged and spaced elongated slits on inner surface of the proximal tubular part. However, the elongated slits are larger in longitudinal direction than the protrusions, thus allowing a certain movement in the longitudinal direction of the pusher member. The inner surface of the pusher member may be provided with a circumferential ledge, which is intended to be in contact with a distally directed end surface of the medicament container. The medicament container positioner mechanism further comprises a spring, arranged between a distal end surface of the pusher member and a washer, in contact with a proximal end surface of the guide member and through which the threaded plunger rod extends.

There are a number of advantages with the present invention. By arranging a plunger rod force means to the threaded plunger rod and by providing the plunger rod force means with tension force as well as torsion force, a combined action is obtained such that when the guide member is in the released state the threaded plunger rod is urged towards the proximal end of the device, and when the guide member is in the locked state the threaded plunger rod is urged towards the distal end of the device.

The force urging the threaded plunger rod in the proximal direction is utilized when a medicament container is to be attached to the device. The threaded plunger rod is then urged towards the distal end of the medicament container by the torsion force and its stopper during the attachment sequence, which means that when the medicament container is in place, the threaded plunger rod has obtained the proper position in relation to the stopper of the medicament container.

Also, when the guide member is in the locked state, then the torsion force is "inactivated" because the guide member, and thus the plunger rod, cannot rotate any more, and the tension force will be the stronger force. Since the tension force acts in the distal direction of the device, it will urge the plunger rod in the distal direction, whereby any play between components of the device will be removed, which in turn will prevent any drooling of the device due to prevailing forces and movement of components after medicament delivery.

Thus preferably a dual function is obtained by one single spring displaying both tensional and torsional properties. The spring is preferably pre-tensioned in order to be able to handle all positions of the plunger rod from a most proximal to a most distal position.

The function of the plunger rod force means is also preferably facilitated by the use of a drive nut threadedly connected to the threaded plunger rod, that in one position, when the guide member is in the release state, is locked so that the threaded plunger rod may be rotated and thus moved in the distal direction, and a second position, when the guide member is in the locked state, where the drive nu can be released by a user, which release causes the threaded plunger rod to be moved linearly in the proximal direction.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

In the present application, when the term "distal part/end" is used, this refers to the part/end of the medicament delivery device, or the parts/ends of the members thereof, which under use of the medicament delivery device is located the furthest away from the medicament delivery site of the patient. Correspondingly, when the term "proximal part/end" is used, this refers to the part/end of the medicament delivery device, or the parts/ends of the members thereof, which under use of the medicament delivery device is located closest to the medicament delivery site of the patient. Further, the term "longitudinal" with or without "axis", when used, refers to a direction or an axis through the device or components thereof in the direction of the longest extension of said device or said component. In a similar manner, the term "transversal" with or without "axis" refers to a direction or an axis through the device or components thereof in a direction generally perpendicular to the longitudinal direction. Also, if nothing else is stated, in the following part of detailed description wherein the mechanical structure of the device and the mechanical interconnection of its components is described, the device is in an initial non-activated or non-operated state.

Mechanical Structure of an Embodiment of a Device

Figure 1:
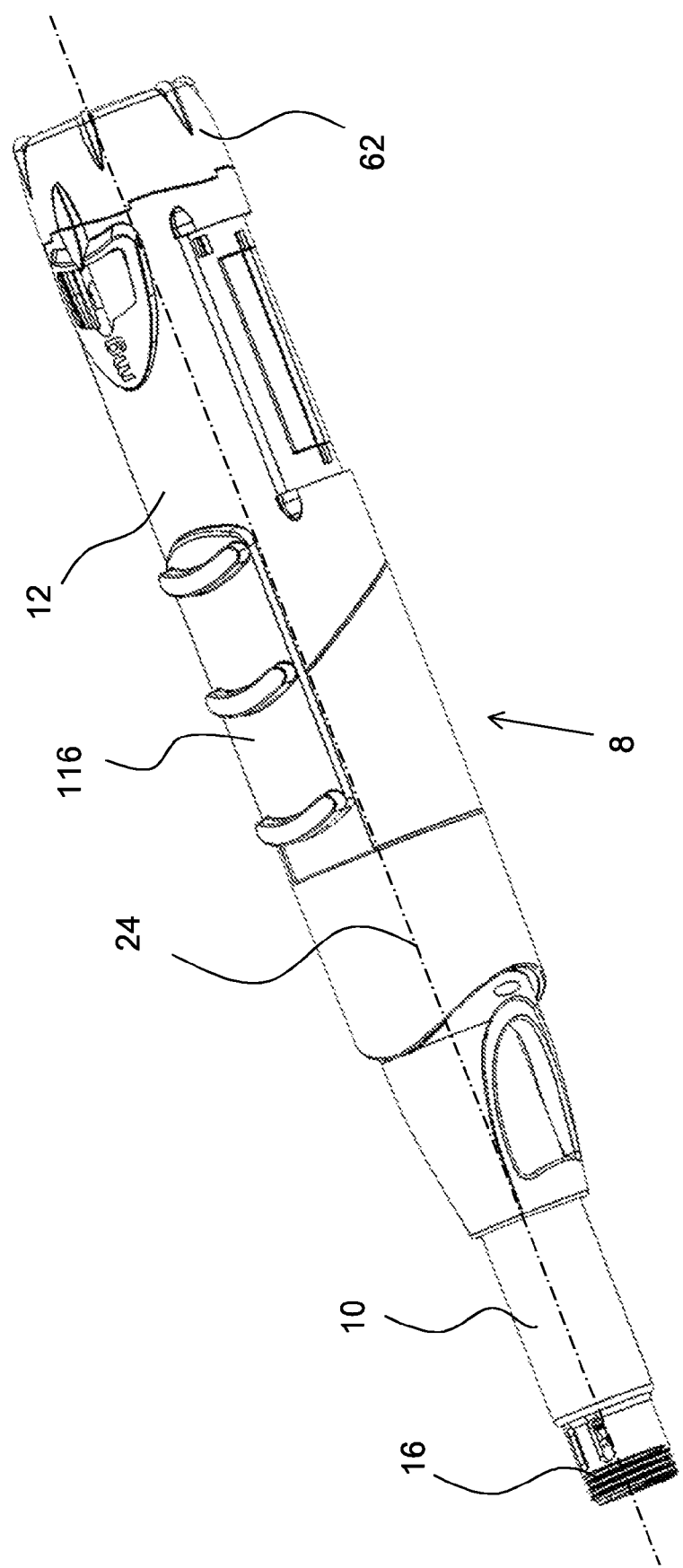
FIG. 1 is a perspective view of a medicament delivery device comprising the present invention.

As seen in the figures, the device according to the invention is arranged with a body 8, FIG. 1, which body comprises a proximal housing part 10 and a distal housing part 12. It is however to be understood that the body 8 may be designed in many other ways. The proximal housing part 10 is arranged as a medicament container holder which accommodates a medicament container 14, FIG. 2, whereby the proximal housing part 10 hereafter will be named medicament container holder. The medicament container 14 is arranged with a movable stopper 15 of a resilient material enclosing a distal end of the medicament container 14. The medicament container holder 10 is further arranged with a neck 16, FIG. 1, at its proximal end for attaching a per se known and conventional injection needle (not shown). The housing parts are arranged with suitable attachment means (not shown) such as bayonet fittings, threads, or the like for attaching the medicament container holder 10 with the distal housing part 12.

Figure 2:
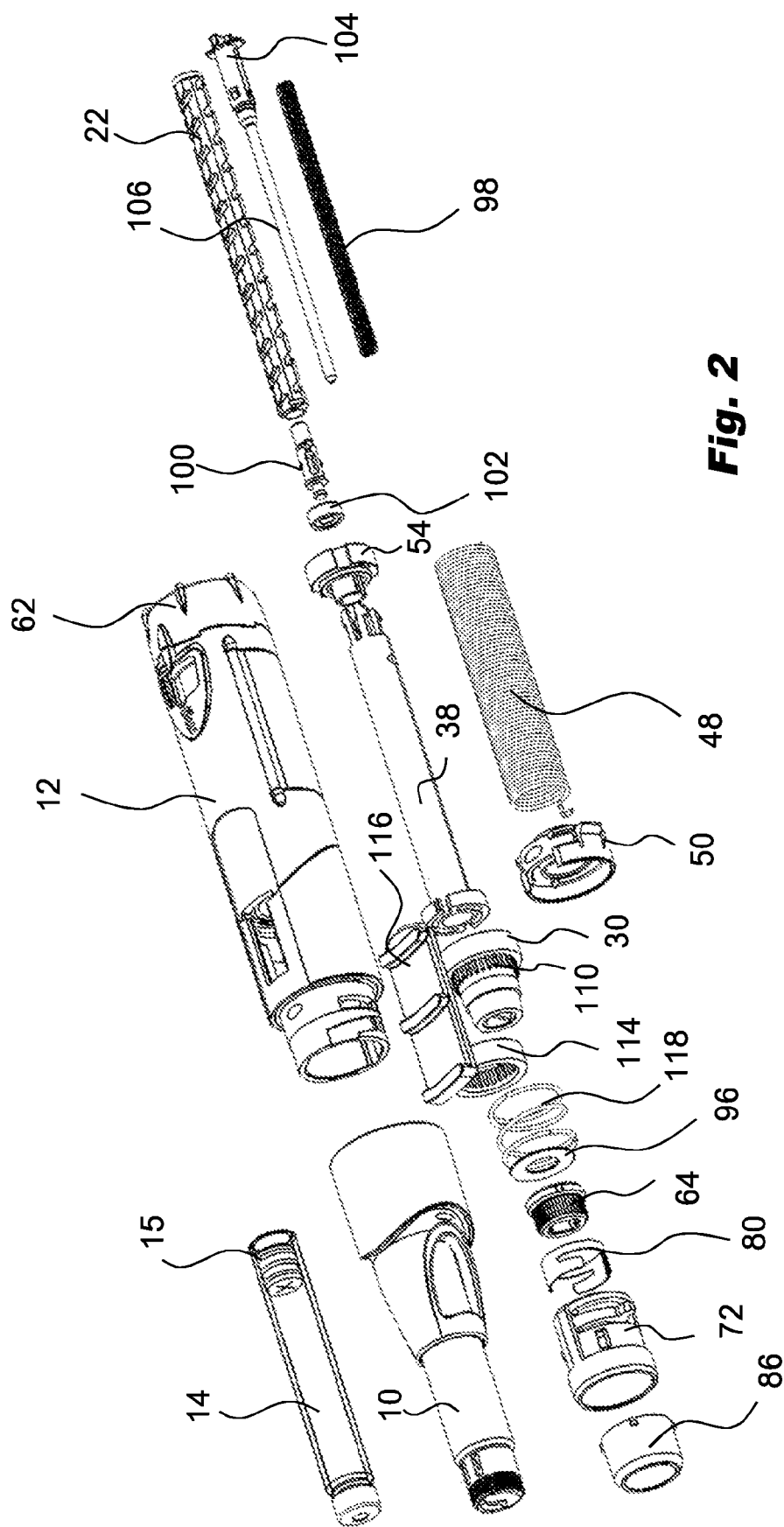
FIG. 2 is an exploded view of the device of FIG. 1.
Figure 5:
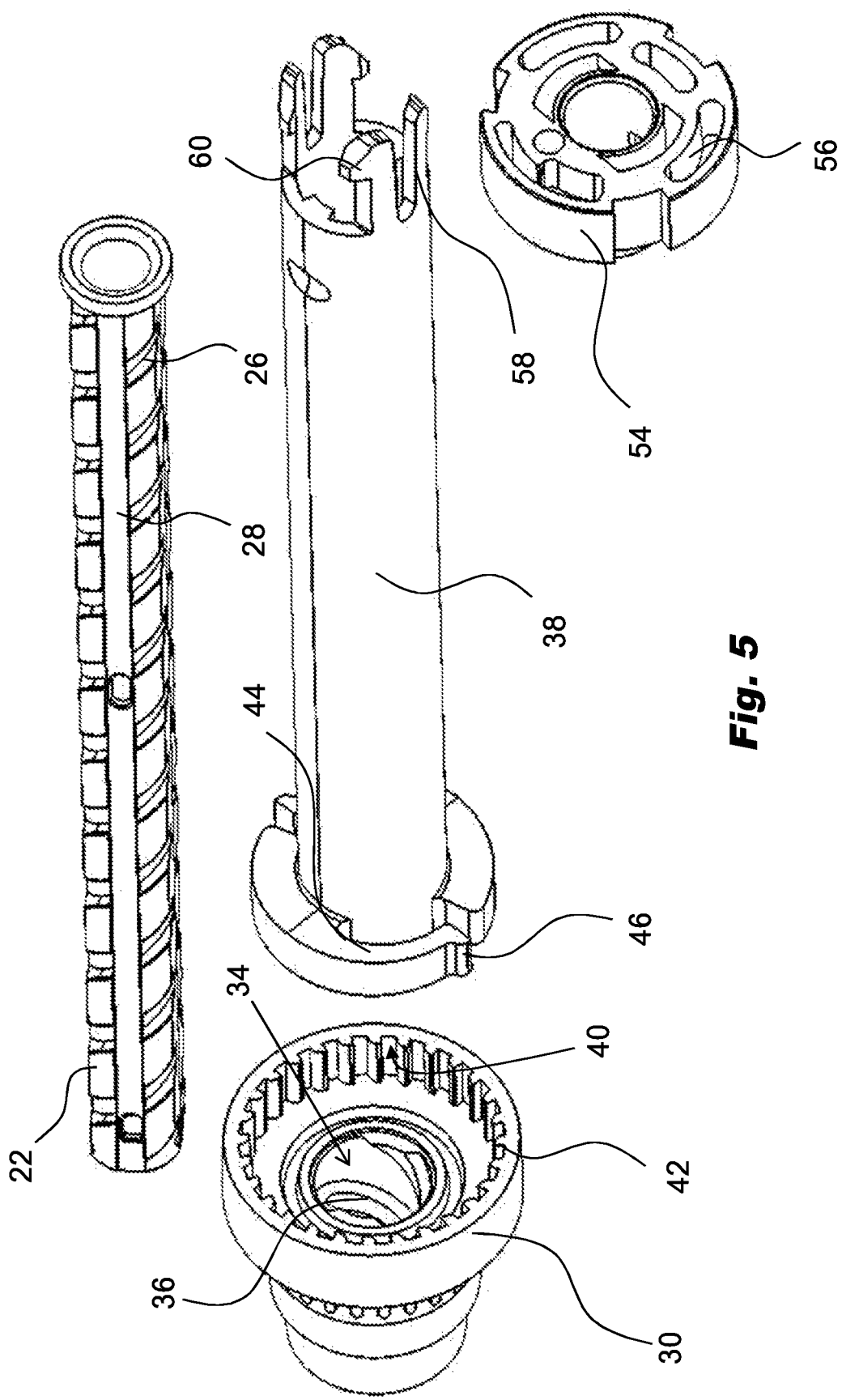

An elongated plunger rod 22, FIGS. 2 and 5, is arranged inside the distal housing part 12, where the plunger rod 22 has a longitudinal axis generally corresponding with the longitudinal direction of the device defined by its longitudinal axis 24, FIG. 1. The plunger rod 22 is arranged with threads 26, FIG. 5, as well as longitudinally extending grooves 28, positioned on opposite sides of the threaded plunger rod 22 as seen in a transversal direction of the threaded plunger rod 22. In the embodiment shown, the threaded plunger rod comprises two opposing longitudinal grooves.

The device further comprises a drive nut 30. The drive nut 30 is configured to drive or move or displace, respectively, the plunger rod 22 as will be described in detail below.

Figure 4:
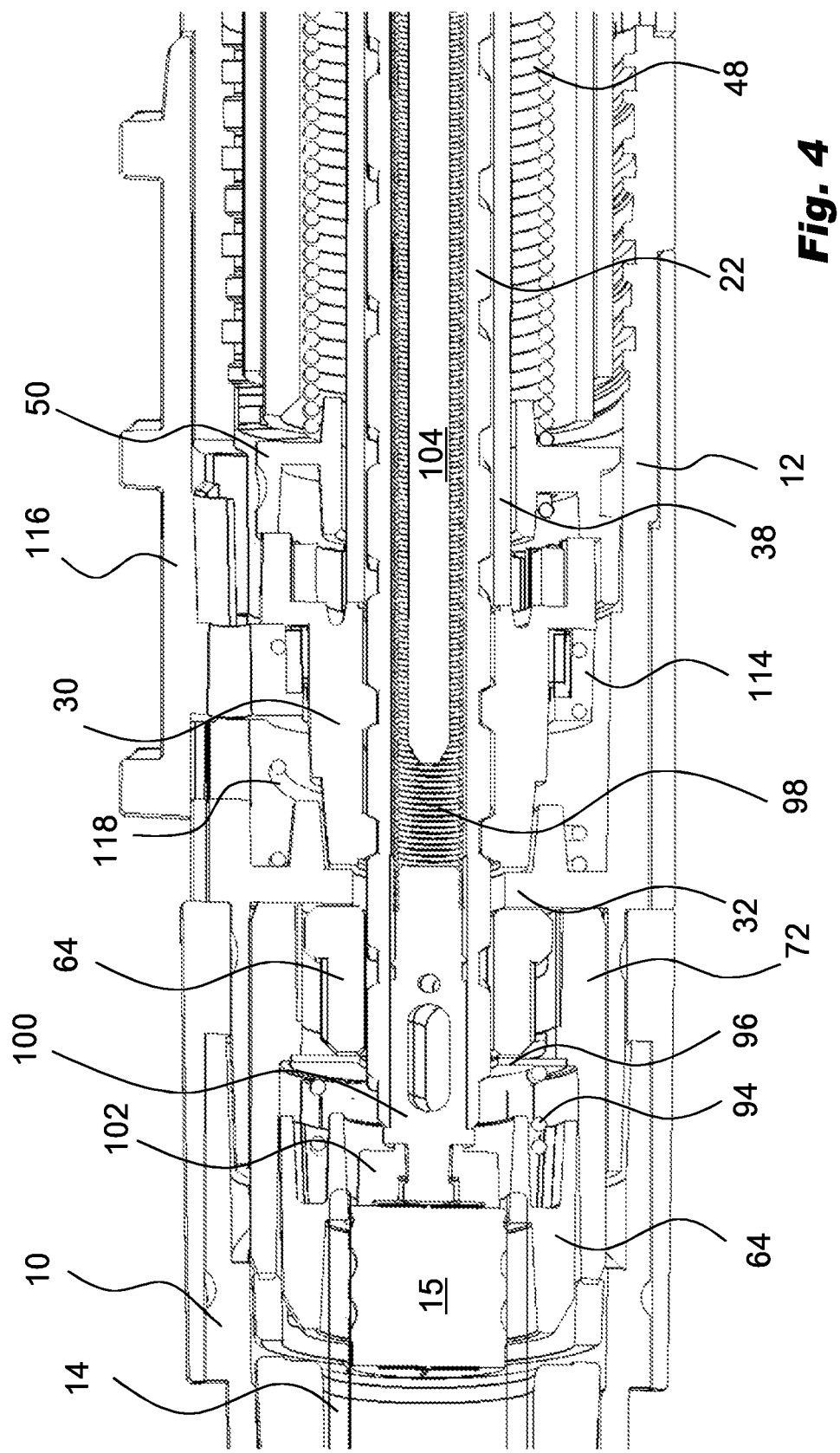
FIG. 4 is a detailed view taken from the area marked IV in FIG. 3, FIGS. 5-9 are detailed views of different components comprised in the device of FIG. 1.

The drive nut 30 has a proximal end surface in contact with a wall 32 of the distal housing part 12, FIG. 4. The wall 32 is located in a proximal area of the distal housing part extends transversally to the longitudinal axis of the device. The wall 32 is provided with a central opening through which the threaded plunger rod 22 extends.

The drive nut 30, FIGS. 2 and 5, is arranged to the threaded plunger rod 22. More particularly, the threaded plunger rod and the drive nut are arranged concentrical. The drive nut 30 is provided with a central opening 34 extending in longitudinal direction, and the threaded plunger rod extends through the central opening 34, FIG. 5. Furthermore, the drive nut 30 comprises threads 36 at least at a circumferential part and at least at a longitudinal part of the surface of the central opening 34 of a corresponding shape and pitch as the threads 26 of the threaded plunger rod 22. Thus, the threads 26 of the threaded plunger rod 22 are engageable by the counter-threads 36 of the drive nut 30 when the plunger rod 22 is arranged such that it extends through the central opening 34. I.e., the drive nut 30 is in threaded engagement with the plunger rod 22.

The device further comprises drive force means configured to drive said drive nut 30. The drive force means comprises a drive shaft 38 of substantially cylindrical configuration, a torsion drive spring 48, a proximal spring attachment member 50, and a distal spring attachment member 54. The connection and the function of the components of the drive force means will be explained below.

Further, the distal end of the drive nut 30 is operably connected to the drive shaft 38, FIG. 5. The connection between the drive nut 30 and the drive shaft 38 comprises an inner circumferential surface 40 on the drive nut 30 provided with a number of wedge-shaped protrusions 42. The inner circumferential surface 40 is located at the distal end of the drive nut 30. The wedge-shaped protrusions 42 extend from the inner circumferential surface 40 towards the center axis of the drive nut 30, i.e. towards the center of central opening 34. Furthermore, the wedge-shaped protrusions 42 extend teeth-like in longitudinal direction of the drive nut 30. Preferably, the protrusions are equidistant. The wedge-shaped protrusions 42 are arranged and shaped to cooperate with arms 44 arranged at a proximal end of the drive shaft 38. The arms 44 extend in a circumferential direction transversal to the longitudinal direction of the drive shaft 38. That is, the arms have a curved shape and extend in a plane being perpendicular to the longitudinal axis of the device. The free ends of the arms 44 are arranged with radially outwardly extending protrusions 46, which protrusions 46 are in contact with, i.e. in operable interaction or engagement with the wedge-shaped protrusions 42 of the drive nut 30. The curved arms are on one of their ends fixed to or connected with the outer surface of the drive shaft 38, whereas the other end of each arm is free. Thus, the arms can be deflected towards the surface of the drive shaft 38 depending on the spacing between the free end of the arm and the outer surface of the drive shaft 38. Such design of the connection enables rotational movement of the drive shaft 38 in one direction relative the drive nut 30 (wherein the arm(s) deflect towards the surface of the drive shaft 38), but a rotational lock between the drive shaft 38 and the drive nut 30 in the opposite rotational direction. Such opposite rotational directions would cause the arms to deflect away from the drive shaft surface which is however prevented by the engagement of the protrusions 46 with the wedge-shaped protrusions 42. In the embodiment shown, the drive shaft comprises two such arms 44.

Figure 6:
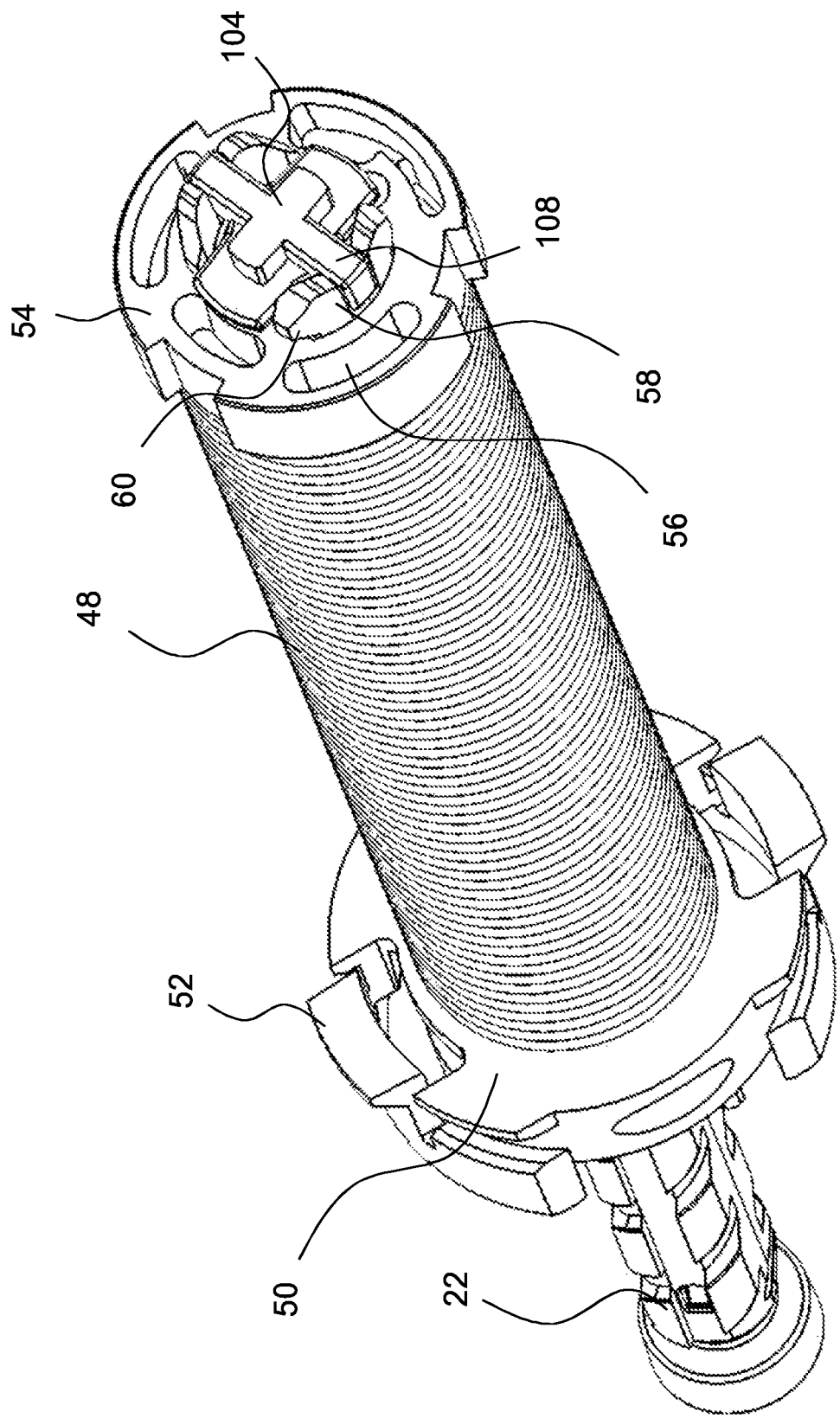

The torsion drive spring 48 of the drive means, FIGS. 2 and 6, is wound surrounding the outer surface of the drive shaft 38. A proximal end of the torsion drive spring 48 is attached to the proximal spring attachment member 50, positioned adjacent and distally of the drive nut 30, FIG. 4. The proximal spring attachment member 50 is fixed to the distal housing part by snap-in tongues 52, FIG. 6, gripping into suitable cut-outs (not shown) of the distal housing part 12. Thus, while the proximal spring attachment member 50 is located distally of the drive nut 30, the drive shaft 38 proximally projects from the proximal spring attachment member 50 in that the arms 44 at the proximal end of the drive shaft 38 extend into the central opening 34 of the drive nut 30 in order to engage with the wedge-shaped protrusions 42 of the drive nut 30. Thus, the proximal spring attachment member is a ring-like element, and the drive shaft 38 passes therethrough.

The torsion drive spring 48 of the drive force means is also provided with a distal end attached to a distal spring attachment member 54, FIGS. 5 and 6. The distal spring attachment member 54 comprises a circular body arranged with a number of passages 56, FIGS. 5 and 6. These passages 56 extend through the distal spring attachment member 54 in longitudinal direction of the device, i.e. from proximal to distal (or vice versa). The drive shaft 38 comprises at its distal end distally extending arms 38, preferably flush with the outer surface of the cylindrical drive shaft 38. Thus, the distally extending arms 38 have a cross-sectional shape, seen in a plane perpendicular to the longitudinal axis of the device, being ring-segment shaped, i.e. curved or rounded. The distally extending arms 58 of the drive shaft 38 pass through some of these passages 56, FIGS. 5 and 6, which passages are as well curved around the center axis. The distal ends of the arms 58 are arranged with transversally directed ledges 60 such that when the arms 58 have been positioned in the passages 56, the ledges 60 contact surfaces of the distal spring attachment member 54 so as to lock the distal spring attachment member 54 to the drive shaft 38. In other words, the drive shaft 38 is snapped onto the distal spring attachment member 54. In the embodiment shown, two arms 58 extend through one passage 56, forming a first arm pair, and another two arms 58 pass through another passage 56 forming a second arm pair. For each pair of arms 58, the ledges 60 extend in opposite directions so that they engage opposing ends of the passage 56. Between the two arms 58 of each pair there is a gap allowing the arms 58 to deflect towards each other when pushed through the passage 56.

The distal spring attachment member 54 is further operably attached to a drive spring tensioner comprising a knob 62, FIGS. 1 and 2, arranged at the distal end of the device such that when the knob 62 is turned, the distal spring attachment member 54 and the drive shaft 38 are turned in relation to the proximal spring attachment member 50 (being fixedly connected to distal housing part 12) as well as the drive nut 30, the latter due to the connection between the drive shaft 38 and the drive nut 30 as described above. The turning action of the knob 62 thus causes a tensioning of the drive spring 48 because the drive spring 48 is on one end connected with the distal spring attachment member 54 which is turned and the on the other end connected to the proximal spring attachment member 50 which is fixed.

Figure 7:
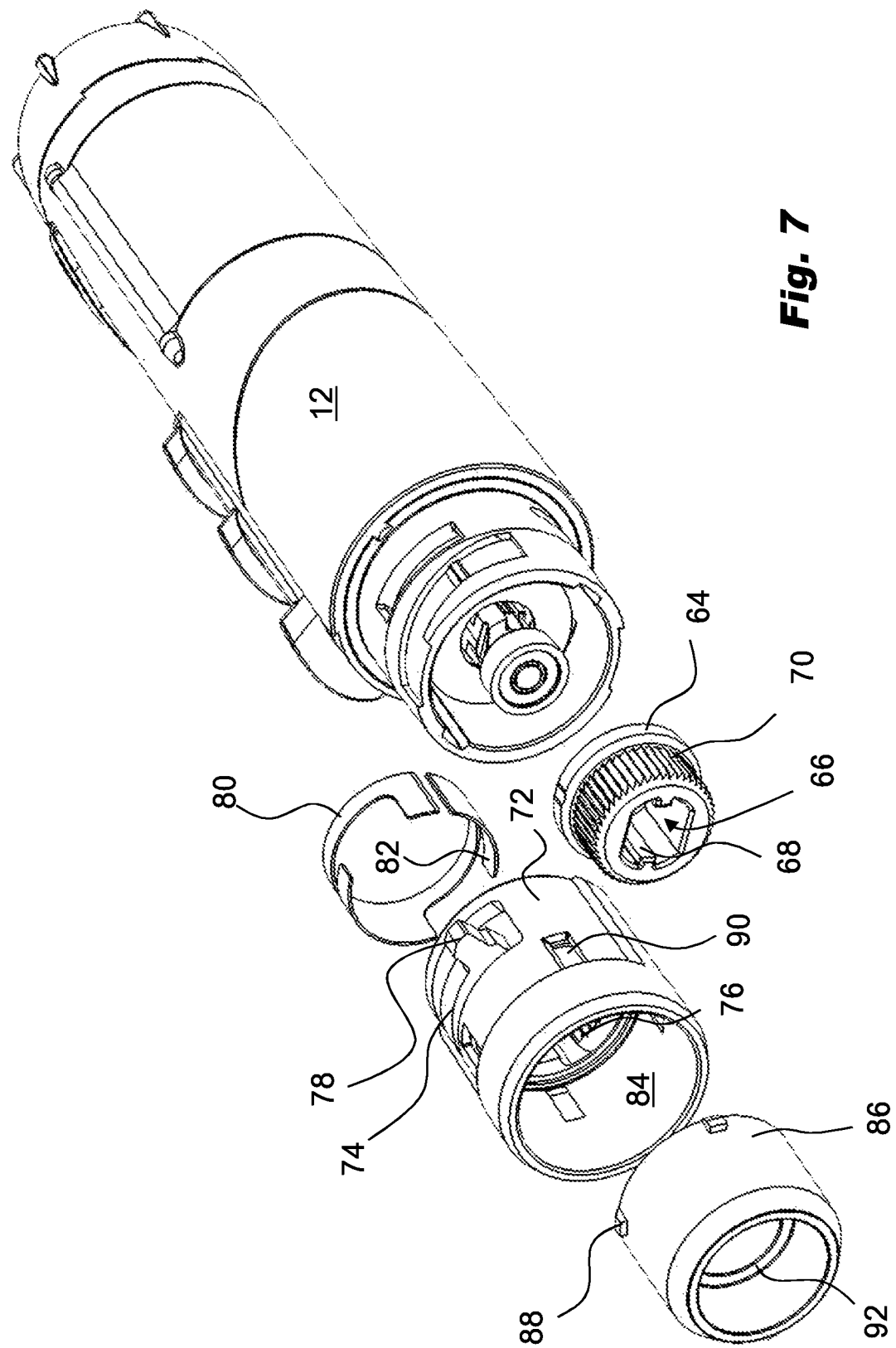

The device according to the invention further comprises a guide member 64, FIGS. 2 and 7, arranged with a central longitudinal passage 66, FIG. 7, in which central passage 66 the threaded plunger rod 22 further fits into. The central passage 66 is arranged with guides 68, FIG. 7, such as radially inwardly directed protrusions and extending in longitudinal direction of the guide member 64. The guides 68 have a shape complementary to the grooves 28 of the threaded plunger rod 22 such as to allow a movement of the plunger rod along the guides 68 in the longitudinal direction but to prevent rotation of the threaded plunger rod 22. An outer circumferential surface of the guide member 64 is arranged with splines 70 or the like ridges, preferably wedge-shaped, FIG. 7, the function of which will be explained below.

Figure 8:
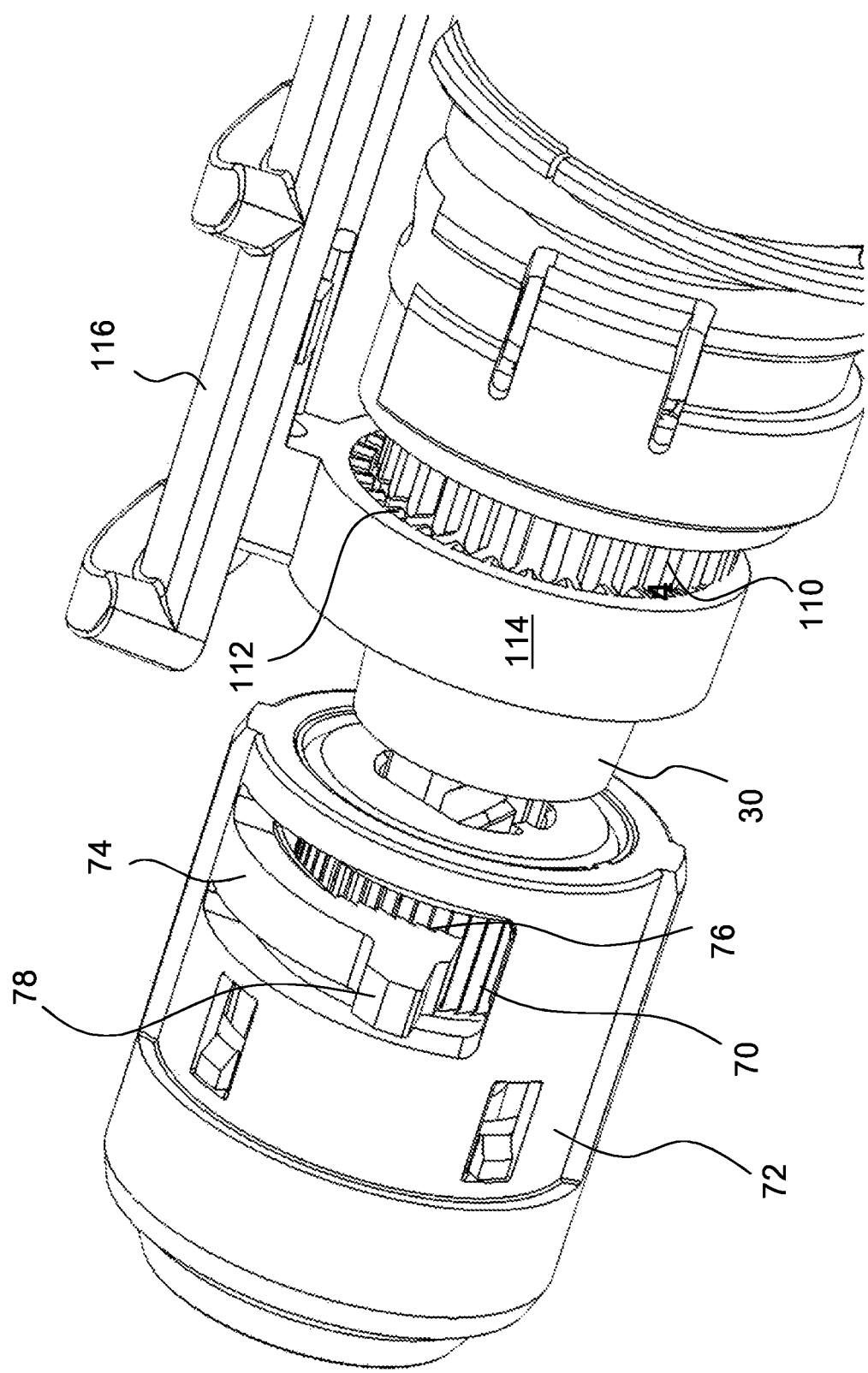

Further a lock and release mechanism is provided, comprising a generally tubular body 72, FIGS. 7 and 8, positioned to surround the splines 70 of the guide member 64, where the body 72 is being arranged with two oppositely positioned arms 74, FIGS. 7 and 8. The arms 74 are extending generally in the circumferential direction of the body 72 and being flexible in the generally radial direction of the body 72. On the inwardly directed surfaces of the arms 74, a number of protrusions 76, preferably wedge-shaped, are arranged, FIGS. 7 and 8, which protrusions 76 preferably have complementary profiles to the splines 70 of the guide member 64. On each of the outwardly directed surfaces of the arms 74, a generally radially outwardly directed ledge 78 is arranged; FIGS. 7 and 8. The ledges 78 are designed such that they come in contact with an inner surface of the medicament container holder 10 when the medicament container holder 10 is attached to the distal housing part 12 such that the arms 74 are forced radially inwards, as will be described.

Further the lock and release mechanism is provided with a ring-shaped resilient member 80, FIG. 7, positioned in the interior of the body 72, which resilient member 80 e.g. may be made of metal having resilient properties. The resilient member 80 is provided with circumferentially extending tongues 82, FIG. 7, which tongues 82 are positioned radially inside the arms 74 of the body 72 and acting to support the arms 74 in flexing them outwards in the radial direction.

The body 72 of the lock and release mechanism extends in the proximal direction with a proximal tubular part 84, FIG. 7, which proximal tubular part 84 is comprised in a medicament container positioner mechanism. The medicament container positioner mechanism comprises a tubularly shaped pusher member 86, FIG. 7, arranged movable in the longitudinal direction inside the proximal tubular part 84. The pusher member 86 is arranged with a number of protrusions 88 on its outer surface in circumferential direction in a plane transverse to the longitudinal axis, FIG. 7. These protrusions 88 fit into correspondingly arranged and spaced elongated slits 90 on inner surface of the proximal tubular part 84. However, the elongated slits 90 are larger in longitudinal direction than the protrusions 88, thus allowing a certain movement in the longitudinal direction of the pusher member 86. The inner surface of the pusher member 86 is provided with a circumferential ledge 92, FIG. 7, which is intended to be in contact with a distally directed end surface of the medicament container 14. The medicament container positioner mechanism further comprises a spring 94, FIG. 4, arranged between a distal end surface of the pusher member 86 and a washer 96, FIG. 4, in contact with a proximal end surface of the guide member 64 and through which the threaded plunger rod 22 extends.

Figure 9:
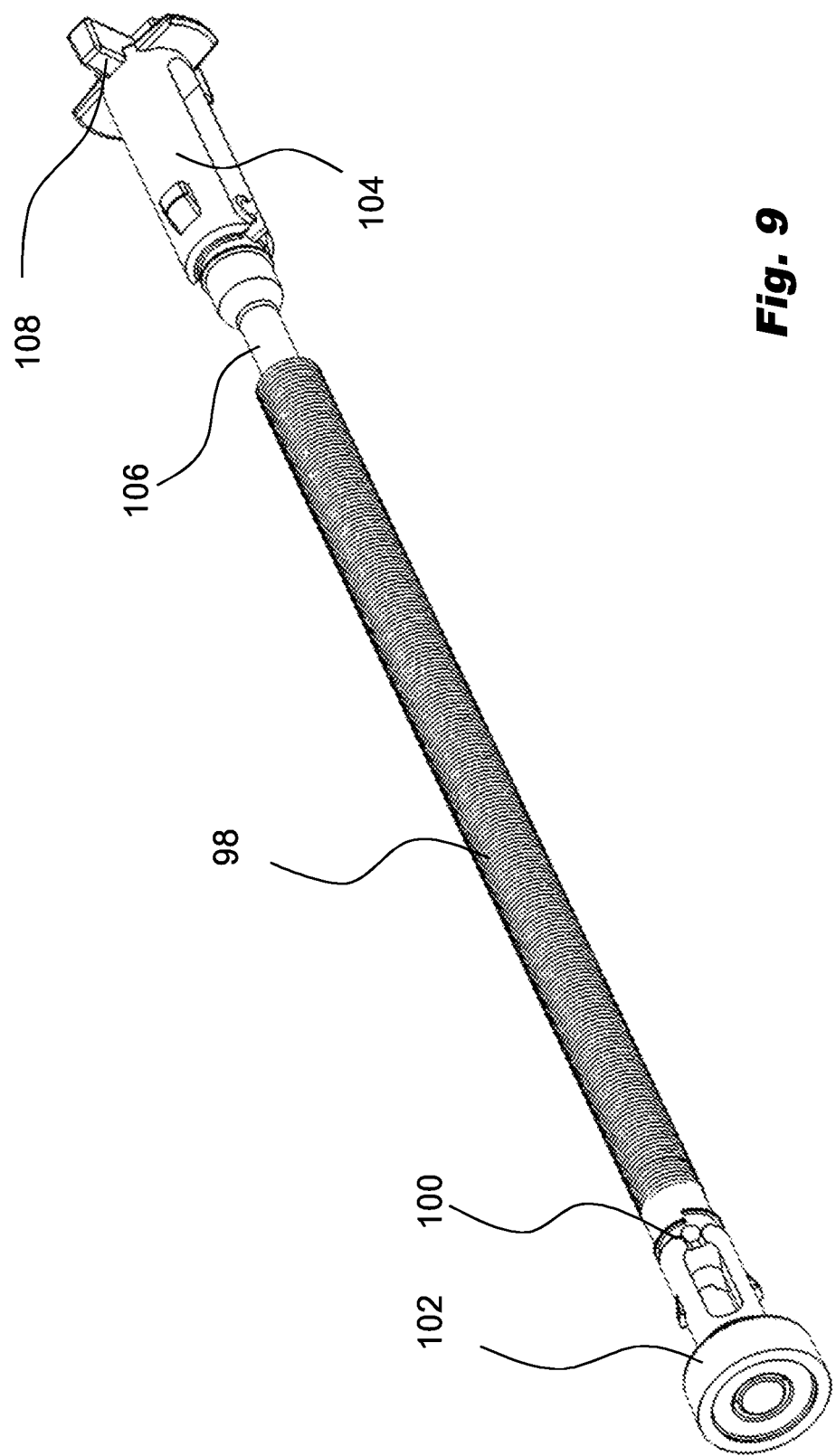

According to the invention, the device is further arranged with a plunger rod force means that in the embodiments shown comprises a spring member 98 having a proximal and a distal end, hereafter named plunger rod control spring, FIGS. 2 and 9. The spring member 98 is pre-tensioned and twisted arranged inside an elongated cavity of the threaded plunger rod 22. A proximal part of the threaded plunger rod or a fixation member 100 comprised in the plunger force means is attached to the proximal end of the threaded plunger rod 22, FIGS. 4 and 9, to which fixation member 100 the proximal end of the plunger rod control spring 98 is attached. At a proximal end of the fixation member 100, a spinner 102, FIGS. 4 and 9, is rotatably arranged.

Further the distal end of the plunger rod control spring 98 is attached to a support member 104, which in its turn is attached to the drive force means as it will be explained below, FIGS. 2 and 9. The support member 104 is arranged extending into the cavity from the distal end of the threaded plunger rod 22. The support member 104 is arranged with a guide pin 106, FIGS. 2 and 9, extending from the support member 104 in the proximal direction inside the plunger rod control spring 98. The function of the guide pin 106 is to prevent buckling of the plunger rod control spring 98.

The support member 104 is further arranged with two oppositely positioned and transversally extending beams 108, FIG. 9. The beams 108 are arranged and designed such that they fit between two of the arms 58 of the drive shaft 38, FIG. 6, i.e. in the gap between the two arms 58, when the arms 58 extend through the distal spring attachment member 54 such that the position of the arms 58 are locked in relation to the distal spring attachment member 54. Thus the support member 104 is also locked to the distal spring attachment member 54 and thus to the drive shaft 38.

Figure 3:
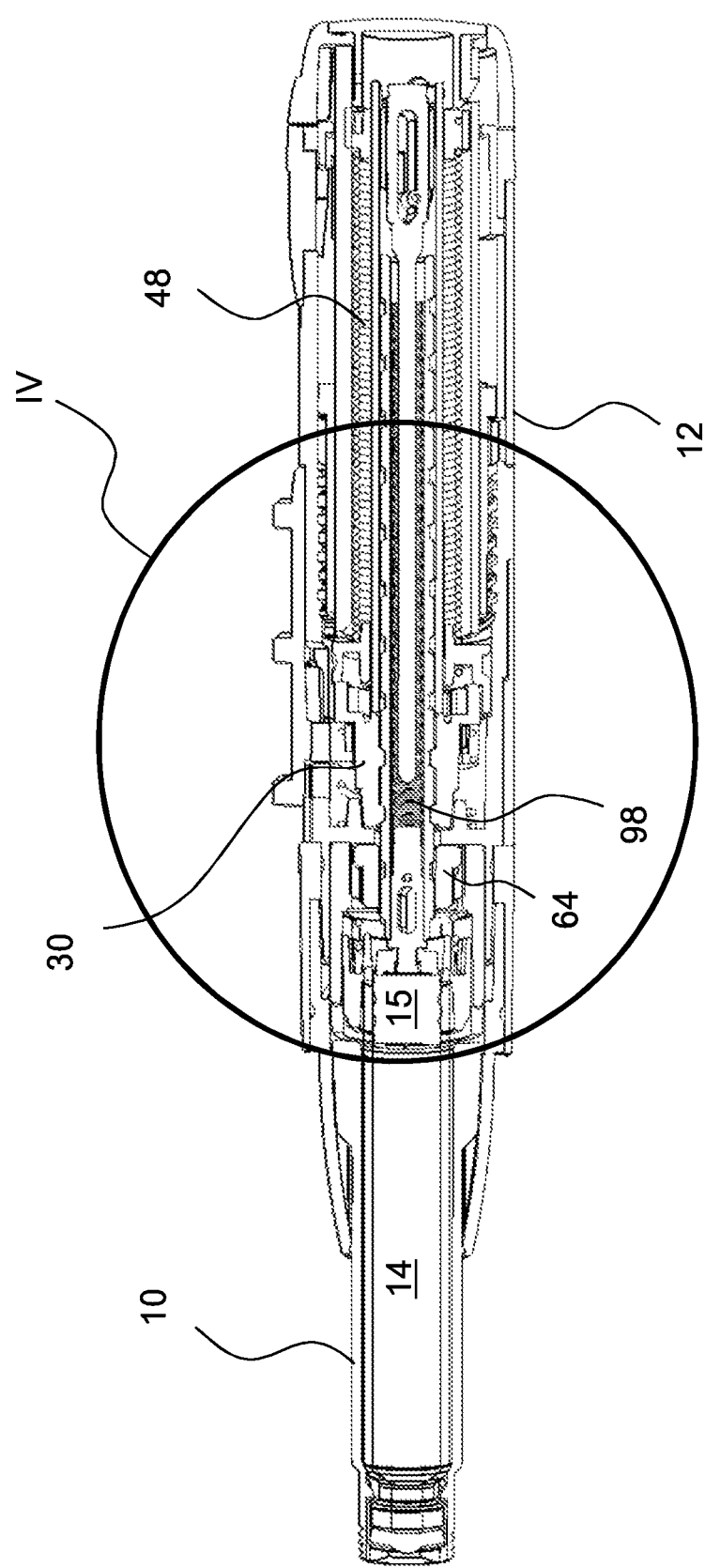
FIG. 3 is a cross-sectional view of the device of FIG. 1.
Figure 10:
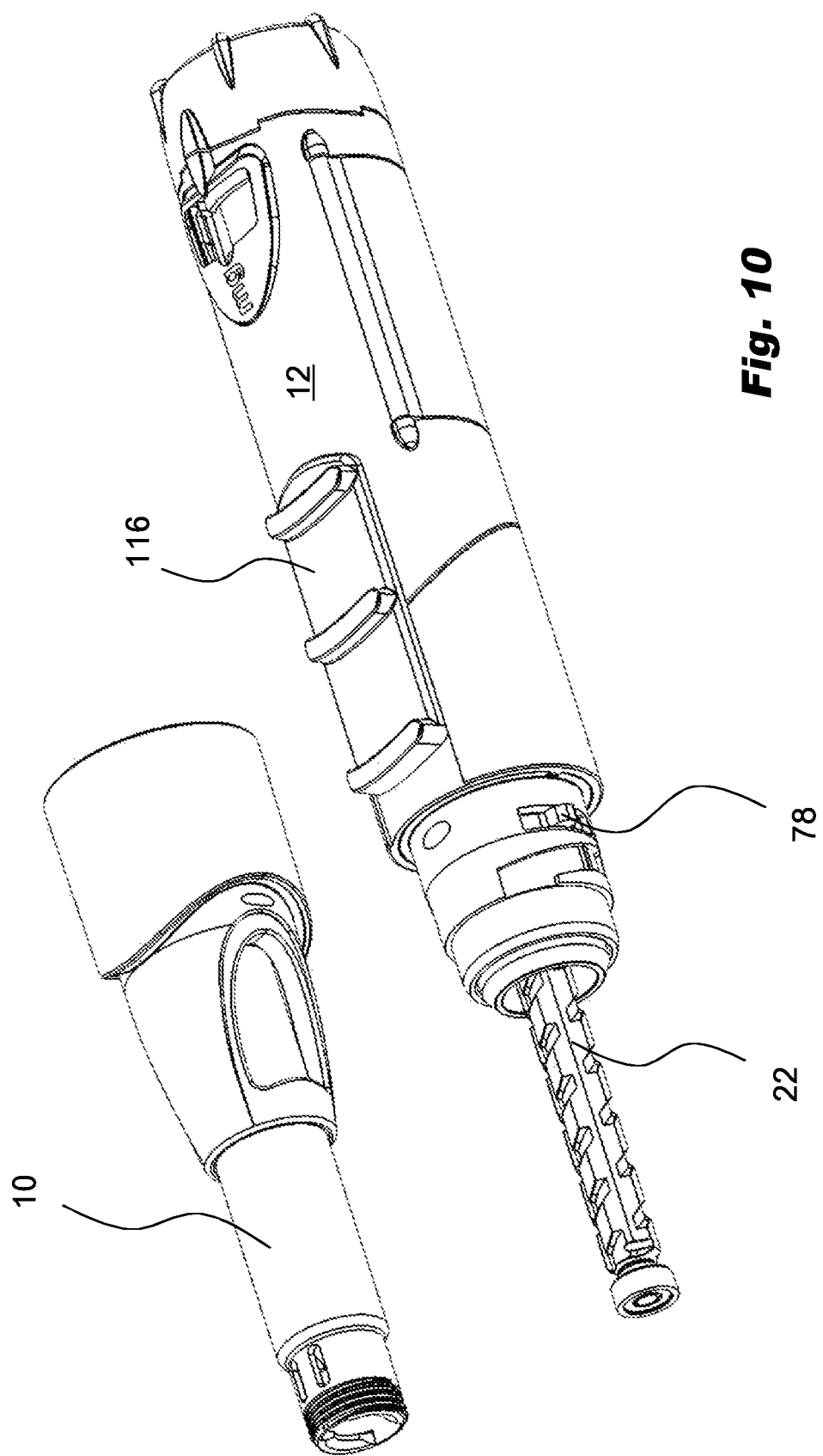
FIG. 10 is a perspective view of the device of FIG. 1 with two housing parts disconnected from each other.

The plunger rod control spring 98 is a tension spring and is chosen such that when the device is assembled, the tension spring displays pulling and torsion properties. When the threaded plunger rod 22 is in an initial, most distal, position, as seen in FIG. 3, the plunger rod control spring 98 causes a pulling force of the threaded plunger rod 22 in the distal direction all the way from its initial most distal position to its most extended proximal position, as seen in FIG. 10. Further, the plunger rod control spring 98 has been twisted during assembly of the device by turning the support member 104 in relation to the drive shaft 38 and the distal attachment member 54 before the beams 108 of the support member 104 are locked between the arms 58 of the drive shaft 38. The twisting of the plunger rod control spring 98 is set such that the torsional force acts on the threaded plunger rod 22 to urge it in the proximal direction all the way from its most extended proximal position, as seen in FIG. 10 to its initial, most distal, position, as seen in FIG. 3.

The drive nut 30 is further operably connected to an actuating mechanism. The actuating mechanism comprises circumferentially extending teeth 110, FIGS. 2 and 8, or protrusions on the outer surface of the drive nut 30. These teeth 110 are arranged to cooperate with mating teeth 112 or protrusions on an inner surface of a ring-shaped member 114 comprised in the actuation mechanism. The actuation mechanism further comprises a manually operated actuation member 116 in the form of a plate or slide button, to which the ring-shaped member 114 is attached. The actuation member 116 is placed on the outer surface of the distal housing part 12, FIG. 1, for access by a user. The actuation mechanism further comprises a spring 118, FIGS. 2 and 4, arranged between the wall 32 and the ring-shaped member 114, urging the ring-shaped member 114 in the distal direction and thereby in engagement with the drive nut 30.

Description of the Function and Operation of Said Embodiment

When the embodiment of the device described above is to be used it has to be prepared for a dose delivery. Initially a medicament container has to be placed inside the device. Therefore, a user grips the medicament container holder 10 as well as the distal housing part 12 and turns them in relation to each other such that the medicament container holder 10 is released from the distal housing part 12. The user then is able of positioning a medicament container 14 inside the container holder 12, whereby the neck of the medicament container 14 is in position inside the neck 16 of the container holder 10.

The user then moves the distal end of the container holder 10, with the distal end of the medicament container 14, towards the proximal end of the distal housing part 12 from where the threaded plunger rod 22 protrudes, FIG. 10. The threaded plunger rod 22 protrudes due to that it is urged in the proximal direction by the plunger rod control spring 98 by the torsional force. This torsional force urges the threaded plunger rod 22 rotationally in the proximal direction when the guide member 64 is in a released state and is free to rotate, where the torsional force is larger than the tension force of the pressure release spring 98. The released state of the guide member 64 is characterized in that the protrusions 76 of the arms 74 of the guide member locking mechanism are out of contact with the splines 70 of the guide member 64 because they flex outwards in the radial direction by the force of the tongues 82 of the resilient member 80, and in that the drive nut 30 is rotationally locked because its teeth 110 are in engagement with the teeth 112 of the ring-shaped member 114 of the actuation mechanism.

When now, during the connection sequence, the plunger rod is to be positioned in relation to the stopper 15 at the distal end of the medicament container 14, the stopper comes in contact with the spinner 102 and acts on the threaded plunger rod 22 in the distal direction, the threaded plunger rod 22 is rotatably threaded back in the distal direction due to the connection with the (currently locked) drive nut 30, where the rotation is facilitated by the spinner 102. The guide member 64 then rotates together with the threaded plunger rod 22 because of the connection between the grooves 28 of the threaded plunger rod and the guides 68 in the central passage 66 of the guide member 64. Further, the rotational movement of the threaded plunger rod 22 in the distal direction will cause the threaded plunger rod control spring 98 to be twisted because its proximal end is attached to the fixation member 100, which in turn is rotationally locked to the threaded plunger rod 22, and because the distal end of the plunger rod control spring 98 is attached to the fixed support member 104, which in turn is locked to the distal spring attachment member 54 as explained above.

When the medicament container holder 10 has been moved in the proper position in relation to the distal housing part 12, the medicament container holder 10 is locked to the distal housing part 12 by suitable attachment means. Because of the contact of the proximal end of the threaded plunger rod 22 with the distal end surface of the stopper 15 of the medicament container 14, the threaded plunger rod 22 is in the correct start position when the device has been prepared for a dose delivery. Thus, the device is now "loaded". The guide member 64 is now locked rotationally because the medicament container holder 10 will act on the ledges 78 of the arms 74 of the lock and release mechanism such that the arms 74 are pushed radially inwards. This causes the inwardly directed protrusions 76 on the arms 74 to engage with the splines 70 of the guide member 64 such that the guide member 64 is in a locked state.

When now the guide member 64 is in the locked state, the tension force of the plunger rod control spring 98 exceeds the torsional force, which tension force tends to pull the threaded plunger rod 22 in the distal direction. The threaded connection between the threaded plunger rod 22 and the drive nut 30 also causes the latter to be pulled in the distal direction, removing any play between the two components. Also any other possible play between components acting on, and being in contact with the drive nut 30, will be removed by the tension force from the pressure release spring 98, pulling the threaded plunger rod 22 in the distal direction.

Further, when the medicament container holder 10 and the distal housing part 12 are connected, the distal end of the medicament container 14 will fit into the pusher member 86 and will come in contact with the ledge 92 inside the pusher member 86. Because of the spring 94 urging the pusher member 86 in the proximal direction, so will also the medicament container 14 be pushed in the proximal direction such that its proximal end surface will come in contact with an inner surface of the medicament container holder 10. Thereby it is ascertained that the medicament container 14 has the proper position in relation to the medicament container holder 10 and thus the neck 16 for attaching a medicament delivery member.

In order to deliver a dose of medicament the knob 62 is turned, which causes the drive shaft 38 to be rotated whereby its arms 44 will slide over the wedge-shaped protrusions 42 of the drive nut 30. The flexibility of the arms 44 and the wedge-shaped protrusions 42 will however prevent rotation back of the drive shaft 38. The rotation of the drive shaft 38 tensions the torsion drive spring 48 because the distal spring attachment member 54, to which the distal end of the torsion drive spring 38 is attached, is turned in relation to the fixed proximal drive spring attachment member 50, to which the proximal end of the torsion drive spring 38 is attached.

In order to deliver a dose of medicament, the user presses the proximal end of the device against a dose delivery site, and in particular an injection site when the medicament delivery member is an injection needle. The actuation member 116 is now manually moved longitudinally in the proximal direction which causes the teeth 112 of the ring-shaped member 114 to move out of contact with the teeth 110 of the drive nut 30. Due to the connection between the drive nut 30 and the drive shaft 38 via its arms 44 acting on the wedge-shaped protrusions 42, the drive nut 30 is free to rotate by the force of the torsion drive spring 48. Due in turn to the threaded connection between the drive nut 30 and the threaded plunger rod 22 as well as the rotational lock of the threaded plunger rod by the guide member 64, the threaded plunger rod 22 is forced linearly in the proximal direction when the drive nut 30 rotates. The movement of the threaded plunger rod 22 in the proximal direction causes the stopper 15 inside the medicament container 14 also to be moved in the proximal direction and a dose of medicament to be expelled through the medicament delivery member.

When the dose delivery operation has been performed by the device, there may be residual forces acting on components inside the device but because of the pulling action of the plunger rod control spring 98 in the distal direction whereby any play has been removed as described above, all movements of components due to residual forces have been removed.

Especially any play that could cause movement of the drive nut 30 acting on the threaded plunger rod 22 with its threads and movement of the drive means acting on the drive nut 30 at an end position of a dose delivery sequence when the threaded plunger rod 22 has been urged in the proximal direction has been removed by the plunger rod control spring 98. Thus, because of the removal of any play between components by the plunger rod control spring 98, all post-delivery movement of the stopper 15 is removed, whereby drooling of medicament from the medicament delivery device is effectively reduced or minimized.

When the container has been emptied, the housing parts are disengaged from each other, the emptied container is removed, a new container is positioned within the medicament container holder and the housing part are attached together as described above.

It is to be understood that the medicament delivery device is preferably a reusable auto-injector.

It is also to be understood that the embodiments described above and shown in the drawings only are to be regarded as non-limiting examples of the invention and that it may be modified in many ways within the scope of the patent claims.

COMPONENTS OF THE DESCRIBED EMBODIMENT

10 proximal housing part, medicament container holder
12 distal housing part
14 medicament container
15 stopper
16 neck of medicament container holder
22 threaded plunger rod
24 longitudinal axis of device
26 threads of threaded plunger rod
28 grooves of threaded plunger rod
30 drive nut
32 wall of distal housing part
34 central opening of drive nut
36 threads of drive nut
38 drive shaft
40 inner circumferential surface of drive nut
42 wedge-shaped protrusions
44 arms of drive shaft
46 protrusions
48 torsion drive spring
50 proximal spring attachment member
52 snap-in tongues
54 distal spring attachment member
56 passages of distal spring attachment member
58 arms of drive shaft
60 ledges of arms of drive shaft
62 knob
64 guide member
66 central passage
68 guides
70 splines
72 body
74 arms of body
76 protrusions
78 ledge of arms
80 resilient member
82 tongues
84 proximal tubular part
88 protrusions
90 slits of proximal tubular part
92 ledge of proximal tubular part
94 spring
96 washer
98 plunger rod control spring
100 fixation member
102 spinner
104 support member
106 guide pin
108 beams of support member
110 teeth of drive nut
112 teeth of ring-shaped member
114 ring-shaped member
116 actuation member
118 spring

The invention claimed is:

1. Medicament delivery device comprising
   a distal housing part, and
   a proximal housing part adapted to receive a medicament container comprising a movable stopper, wherein said housing parts are configured to be attached to each other;
   a threaded plunger rod arranged within said medicament delivery device and being movable in a longitudinal direction of the device;
   a drive nut configured to drive said threaded plunger rod towards a proximal end of the device; and
   a spring is pre-tensioned and twisted arranged inside the threaded plunger rod and operably associated with said threaded plunger rod and configured to exert both a torsion force and a tension force on said threaded plunger rod for positioning the plunger rod in relation to the stopper and for avoiding drooling respectively.

2. Medicament delivery device of claim 1, further comprising a drive force configured to drive said drive nut.

3. Medicament delivery device of claim 1, further comprising
   a guide member rotatably lockable but longitudinally slidably connected to said threaded plunger rod and configured to be switched by a lock and release mechanism between
   a locked state in which the guide member is prevented to rotate when said housing parts are connected to each other and
   a released state in which the guide member is allowed to rotate when said housing parts are disconnected.

4. Medicament delivery device according to claim 3, wherein the torsion force acting on the threaded plunger rod when said guide member is in the released state, exceeds the tension force such that said threaded plunger rod is urged towards the proximal end of the device, and wherein the tension force acting on said threaded plunger rod when said guide member is in the locked state exceeds the torsion force such that the threaded plunger rod is urged towards a distal end of the device.

5. Medicament delivery device according to claim 1, wherein said threaded plunger rod is configured to act on said stopper.

6. Medicament delivery device according to claim 1, wherein the spring has a proximal end attached to a proximal fixation member and a distal end attached to a support member.

7. Medicament delivery device according to claim 1, wherein said spring displays pulling and torsion properties.

8. Medicament delivery device according to claim 1, wherein said spring comprises a tension spring.

9. Medicament delivery device according to claim 3, wherein the device further comprises an actuation mechanism which is operably connected to said drive nut such that said drive nut is locked when said guide member is in the released state.

10. Medicament delivery device according to claim 9, wherein said actuation mechanism further comprises
- a manually operable actuation member, capable of, upon operation, releasing said drive nut and thus said drive means for driving said threaded plunger rod towards a proximal end of the device.

11. Medicament delivery device according to claim 6, wherein a proximal part of said proximal fixation member is connected with a proximal end of the threaded plunger rod.

12. Medicament delivery device according to claim 6, wherein said support member is connected to a drive force configured to drive a drive nut.

13. Medicament delivery device of claim 1, further comprising a rotatable drive shaft and a torsion drive spring,
- wherein rotation of the drive shaft causes said torsion drive spring to tension.

14. Medicament delivery device of claim 13, wherein said torsion drive spring force acts on said threaded plunger rod in that actuation of the medicament delivery device causes the threaded plunger rod to move in a longitudinal direction on account of the tension of said torsion drive spring.

15. Medicament delivery device of claim 1, wherein the device comprises a reusable auto-injector.

* * * * *